United States Patent
Niwa et al.

(10) Patent No.: US 7,671,996 B2
(45) Date of Patent: Mar. 2, 2010

(54) SURFACE PLASMON RESONANCE SENSOR AND BIOCHIP

(75) Inventors: Daisuke Niwa, Kyoto (JP); Dai Ohnishi, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 0 days.

(21) Appl. No.: 12/206,022

(22) Filed: Sep. 8, 2008

(65) Prior Publication Data

US 2009/0066962 A1    Mar. 12, 2009

(30) Foreign Application Priority Data

Sep. 10, 2007    (JP)    ............... 2007-234289

(51) Int. Cl.
*G01N 21/00* (2006.01)
(52) U.S. Cl. ..................................... 356/445
(58) Field of Classification Search .......... 356/445–448
See application file for complete search history.

(56) References Cited

U.S. PATENT DOCUMENTS

| 7,271,914 | B2 * | 9/2007 | Lin et al. ..................... 356/445 |
| 2003/0137772 | A1 * | 7/2003 | Challener ................... 360/131 |
| 2006/0274314 | A1 * | 12/2006 | Thomsen et al. ............ 356/445 |
| 2009/0052827 | A1 * | 2/2009 | Durfee et al. ................. 385/2 |

FOREIGN PATENT DOCUMENTS

JP    2003-042944    2/2003
JP    2003-279476    10/2003

OTHER PUBLICATIONS

Kurihara et al. (2002) "Theoretical understanding of an absorption-based surface Plasmon resonance sensor based on Kretchmann's theory." Anal. Chem. 74(3):696-701, Abstract only.
Shumaker-Parry et al. (2004) "Microspotting streptavidin and double-stranded DNA arrays on gold for high-throughput studies of protein-DNA interactions by surface plasmon resonance microscopy." Anal. Chem. 76(4):918-929, Abstract only.
Nakanotani et al. (2007) "Extremely Low-Threshold Amplified Spontaneous Emission of 9,9'-Spirobifluorene Derivatives and Electroluminescence from Field-Effect Transistor Structure." Adv. Funct. Mater. pp. 1-8.

* cited by examiner

*Primary Examiner*—Michael P Stafira
(74) *Attorney, Agent, or Firm*—Fish & Richardson P.C.

(57) ABSTRACT

The present invention relates to a surface plasmon resonance sensor which has a first dielectric layer, a metal layer disposed on the first dielectric layer, and a second dielectric layer covering the metal layer. The surface plasmon resonance sensor includes: a sensor main body provided with an opening for exposing a part of a surface of the metal layer on a side facing the second dielectric layer, and for allowing a measurement sample to be brought into contact with this surface; a light source for introducing a beam into the metal layer from one end of the metal layer in a longitudinal direction of the metal layer; and a detection unit detecting a beam emitted from the other end of the metal layer, has high sensitivity in measurement, is downsized, and is usable in a simple manner.

9 Claims, 8 Drawing Sheets

SURFACE PLASMON RESONANCE SENSOR AND BIOCHIP

BACKGROUND OF THE INVENTION

1. Field of the Invention

The present invention relates to a surface plasmon resonance sensor that utilizes a surface plasmon resonance phenomenon, and particularly relates to a small-size surface plasmon resonance sensor. Further, the present invention relates to a biochip that utilizes this surface plasmon resonance sensor.

2. Description of the Background Art

At present, in the fields of biochemistry and medicine, there is an increasing demand to elucidate with high precision a correlation between physiologically active molecules or the like in a living body. Therefore, small-size sensors capable of measuring with high precision a process or the like of a biochemical reaction of physiologically active molecules or the like have been demanded, and research has been conducted thereon. Among methods used by these sensors, a method that uses a light in measurement is superior in sensitivity, and many schemes such as a calorimetric method, a fluorometric method, and a luminescent method have been developed. However, sensors that use these schemes become large in size, and furthermore, it is reported that a quenching phenomenon due to dye fading may occur. In addition, only sluggish improvement can be achieved in sensitivity of measurement by these schemes. Moreover, the sensors mainly used at present are often configured to conduct measurement in a state where measurement samples are dispersed in a solution. With this configuration, these sensors require a certain optical path length or longer, and this makes it difficult to downsize the sensors.

Figure 10:
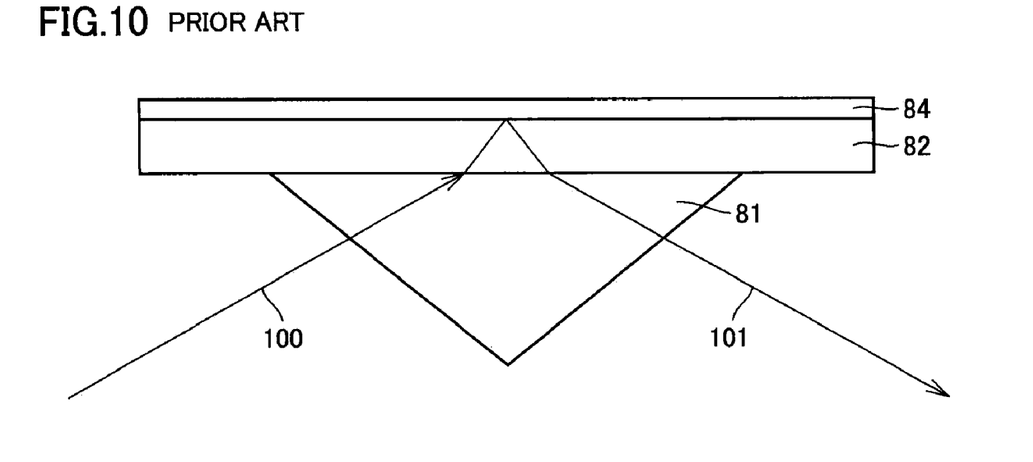
FIG. 10 is a schematic cross-sectional view that shows a surface plasmon resonance phenomenon.

Accordingly, there have recently been proposed sensors that utilize a sensing method of measuring a reaction occurring at a surface of, or a periphery of the surface of, a substrate onto which living body molecules are fixed. In particular, a sensor that uses surface plasmon resonance spectroscopy is superior in sensitivity and can be downsized as well, and hence attracts attention (e.g. see K. Kurihara et al. Anal Chem. 74 (3): 696-701 (2002) and Shumaker-Parry J S et al. Anal Chem. 76 (4): 918-929 (2004)). Here, FIG. 10 is a schematic cross-sectional view that shows a surface plasmon resonance phenomenon. A description will now be made based on FIG. 10.

An incident beam 100 is incident on a dielectric substrate 82 covered with a metal film 84 through a prism 81. Incident beam 100 passes through dielectric substrate 82 to be reflected by metal film 84, so that an emitted beam 101 is generated through prism 81. At this time, when a certain incident angle and a certain reflection angle are set for operations of incident beam 100 and emitted beam 101, surface plasmon resonance is observed at an interface between metal film 84 and dielectric substrate 82. A surface plasmon resonance sensor that has the configuration shown in FIG. 10 is now under development (e.g. see Japanese Patent Laying-Open No. 2003-279476 and Japanese Patent Laying-Open No. 2003-42944).

However, in the currently-used surface plasmon resonance sensor, it is necessary to dispose a chip and an optical system such that a certain incident angle and a certain reflection angle are achieved, in order to allow incident beam 100 to be incident through prism 81 or a transparent substrate made of quartz or the like, and hence drastic downsizing is difficult.

SUMMARY OF THE INVENTION

As described above, sensors with small size and high sensitivity in measurement are demanded at present in the fields of biochemistry and medicine.

Further, research has also been conducted on sensors that detect olfactory sense-related substances with high sensitivity in a simple manner, in addition to the sensors in the fields of biochemistry and medicine. For example, even at present, drug detection at the airport and the like still mainly relies upon the olfactory sense of dogs.

In view of the problems described above, an object of the present invention is to provide a surface plasmon resonance sensor that has high sensitivity in measurement, is downsized, and is usable in a simple manner.

The present invention relates to a surface plasmon resonance sensor which has a first dielectric layer, a metal layer disposed on the first dielectric layer, and a second dielectric layer covering the metal layer. The surface plasmon resonance sensor includes: a sensor main body provided with an opening for exposing a part of a surface of the metal layer on a side facing the second dielectric layer, and for allowing a measurement sample to be brought into contact with the surface; a light source for introducing a beam into the metal layer from one end of the metal layer in a longitudinal direction of the metal layer; and a detection unit detecting a beam emitted from the other end of the metal layer.

Further, in the surface plasmon resonance sensor of the present invention, it is preferable that the metal layer is made of any of materials selected from gold, silver, aluminum, copper, titanium, nickel, and chromium.

Further, in the surface plasmon resonance sensor of the present invention, it is preferable that the metal layer has a thickness ranging from 1 nm to 100 nm.

Further, in the surface plasmon resonance sensor of the present invention, it is preferable that a refractive index of each of the first dielectric layer and the second dielectric layer falls within a range of 1.0 to 4.0.

Further, in the surface plasmon resonance sensor of the present invention, it is preferable that the sensor main body is provided on a substrate made of any of materials selected from $SiO_2$, GaAs, InP, Si, glass, quartz, silicone, and plastic.

Further, in the surface plasmon resonance sensor of the present invention, it is preferable that the light source causes a laser beam to be incident.

Further, in the surface plasmon resonance sensor of the present invention, it is preferable that the measurement sample is in a liquid state or a gaseous state.

Further, in the surface plasmon resonance sensor of the present invention, it is preferable that the metal layer has a linear shape or an approximately L-shape.

Further, in the surface plasmon resonance sensor of the present invention, it is preferable that living body molecules are fixed onto the metal layer in the opening of the second dielectric layer, and that the measurement sample is brought into contact with the living body molecules.

Further, in the surface plasmon resonance sensor of the present invention, it is preferable that the surface of the metal layer in the opening of the second dielectric layer is subjected to a molecular modification process for fixing the living body molecules.

Further, in the surface plasmon resonance sensor of the present invention, it is preferable that target molecules contained in the measurement sample and reacting with the living body molecules are modified with nanoparticles, and that the nanoparticles contain at least one of gold, silver, aluminum, copper, titanium, nickel, and chromium, and have an average particle diameter ranging from 1 nm to 1 μm.

Further, in the surface plasmon resonance sensor of the present invention, it is preferable that aggregates made of the living body molecules and the target molecules are fixed to the surface of the metal layer.

Further, in the surface plasmon resonance sensor of the present invention, it is preferable that it is possible to measure an antigen-antibody reaction, a genetic mutation, an interaction between genes and proteins, functions of cells and proteins, an enzyme reaction, and a metabolic substance.

Further, the present invention relates to a biochip provided with the surface plasmon resonance sensor described above.

The surface plasmon resonance sensor of the present invention utilizes a surface plasmon wave generated by allowing a beam to be directly incident on the metal layer, so that it enables measurement with sensitivity higher than that of the conventional surface plasmon resonance sensor by a few orders of magnitude. Therefore, by using the surface plasmon resonance sensor of the present invention in the fields of biochemistry and medicine, the surface plasmon resonance sensor enables highly precise detection and diagnosis such as identification of an antigen-antibody reaction, a genetic mutation, interactions between genes, between proteins, and between genes and proteins, functions of cells and proteins, and a metabolic substance. Further, this surface plasmon resonance sensor is expected to be variously applied to, for example, drug testing, a freshness test for food, measurement of a toxic substance concentration, and the like.

In the surface plasmon resonance sensor of the present invention, the light source and the sensor main body can be disposed on the same plane, so that significant downsizing of the measurement system can be achieved. Accordingly, highly precise measurement, which has only been allowed in a laboratory and in a sophisticated facility such as a university hospital, can be conducted anywhere.

Further, by fabricating a biochip in which the light source, the sensor main body, and the detection unit are integrated, it is possible to provide an unprecedented simple sensing tool.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the present invention will hereinafter be described based on the drawings. Note that the same or corresponding portions in the drawings below are provided with the same reference characters, and the description thereof will not be repeated. Further, the dimensions such as a length, a size, and a width in the drawings are modified as appropriate for the sake of clarity and simplicity of the drawings, and do not represent actual dimensions.

First Embodiment

Figure 1:
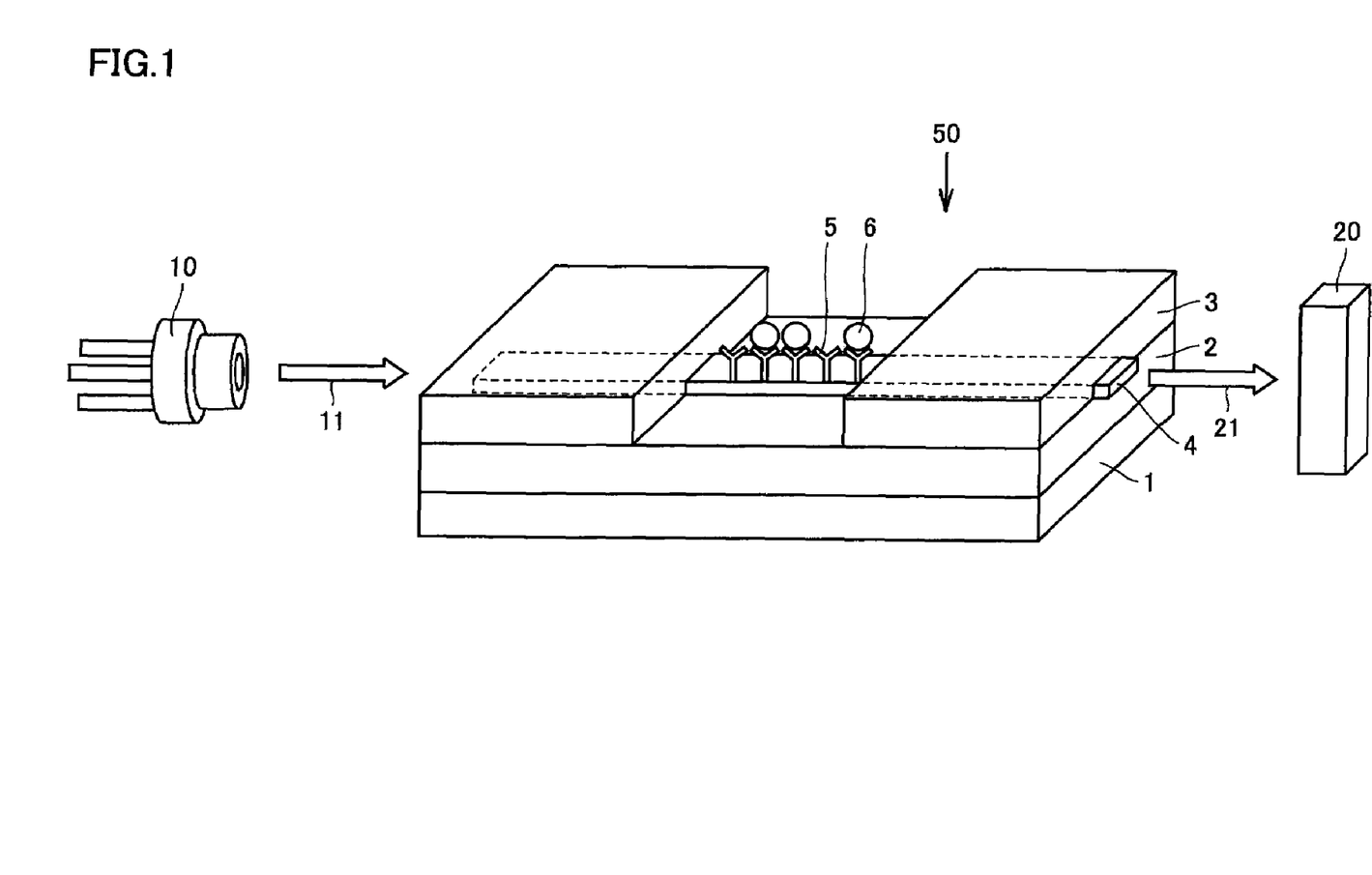
FIG. 1 is a schematic perspective view that shows an embodiment of the present invention.
Figure 2:
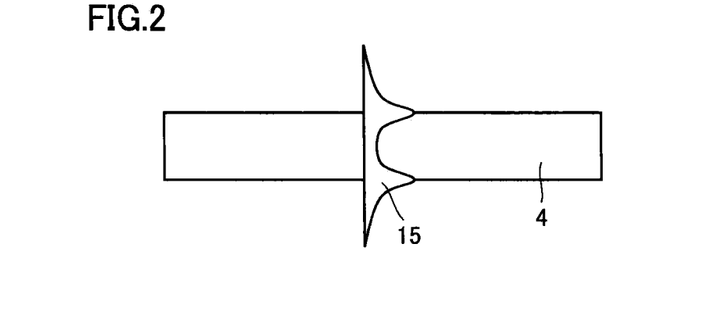
FIG. 2 is a schematic cross-sectional view that shows a surface plasmon wave generated at a metal layer in the present invention.

FIG. 1 is a schematic perspective view that shows an embodiment of the present invention. FIG. 2 is a schematic cross-sectional view that shows a surface plasmon wave generated at a metal layer in the present invention. In the following, a basic structure of a surface plasmon resonance sensor of the present invention will be described based on FIG. 1, and generation of a surface plasmon wave in the surface plasmon resonance sensor of the present invention will be described based on FIG. 2.

<<Structure>>

As shown in FIG. 1, the surface plasmon resonance sensor of the present invention includes a sensor main body 50, a laser 10 that serves as a light source, and a detection unit 20. Sensor main body 50 has at least a first dielectric layer 2, a metal layer 4 disposed on first dielectric layer 2, and a second dielectric layer 3 that covers metal layer 4. In the present embodiment, sensor main body 50 is provided on a substrate 1. Sensor main body 50 is provided with an opening for exposing a part of a surface of metal layer 4 on a side facing second dielectric layer 3, and for allowing a measurement sample to be brought into contact with this surface. In the present embodiment, antibodies 5 identified as living body molecules that react with target molecules contained in the measurement sample are fixed to metal layer 4 in this opening. Laser 10 emits a laser beam 11 and introduces laser beam 11 into metal layer 4 from its one end in a longitudinal direction of metal layer 4. Laser beam 11 travels through metal layer 4 that serves as a waveguide along its longitudinal direction, and is emitted from the other end of metal layer 4. Detection unit 20 detects an emitted beam 21 that has been emitted from the other end.

A refractive index of a periphery of an upper surface of metal layer 4 varies before and after the measurement sample is brought into contact with the opening. In the present invention, target molecules in the measurement sample are measured by analyzing changes in this refractive index by means of detection unit 20 that detects emitted beam 21. It is preferable that an area of metal layer 4 that does not face this opening is completely covered with second dielectric layer 3. However, a portion of such an area may not be covered therewith.

Metal layer 4 preferably has a thickness ranging from 1 nm to 100 nm, and particularly preferably has a thickness ranging from 10 nm to 40 nm. This is because if metal layer 4 has a thickness of less than 1 nm, it may be difficult to form metal layer 4, and if metal layer 4 has a thickness exceeding 100 nm, surface plasmon resonance may not occur at metal layer 4. Further, metal layer 4 preferably has a length in a transverse direction ranging from 100 nm to 100 µm. This is because if this length is less than 100 nm, surface plasmon resonance may not occur at metal layer 4, and if this length exceeds 100 µm, many high-order surface plasmon waves that are difficult to use may occur. Further, metal layer 4 preferably has a length in a longitudinal direction ranging from 30 µm to 5 mm. This is because if this length is less than 30 µm, sufficient resolution (analyzing power) may not be obtained, and if this length exceeds 5 mm, intensity of emitted beam 21 may become too low to be detected by detection unit 20.

This opening is preferably provided to have a length in a longitudinal direction ranging from 10 µm to 5 mm. This is because if the length is less than 10 µm, a quantity by which the measurement sample is brought into contact therewith may be insufficient, and if the length exceeds 5 mm, intensity of emitted beam 21 may become too low to be detected.

Further, a refractive index of each of first dielectric layer 2 and second dielectric layer 3 is preferably set to fall within a range of 1.0 to 4.0. Further, it is preferable that the refractive index of first dielectric layer 2 and the refractive index of second dielectric layer 3 are approximately the same. Note that thicknesses of first dielectric layer 2 and second dielectric layer 3 are not particularly limited. For example, both of first dielectric layer 2 and second dielectric layer 3 may have thicknesses ranging from 100 nm to 100 µm.

A material of metal layer 4 is preferably any material selected from gold, silver, aluminum, copper, titanium, nickel, and chromium. This is because these materials have a property of easily generating a surface plasmon wave.

Further, a material of each of first dielectric layer 2 and second dielectric layer 3 is preferably any material selected from $SiO_2$, GaAs, InP, Si, glass, quartz, silicone, and plastic. This is because these materials have high translucency, and are unlikely to absorb laser beam 11 from laser 10.

Further, examples of the living body molecules fixed onto metal layer 4 in the opening provided in second dielectric layer 3 can include proteins such as antibodies and enzymes, DNAs, and the like. Examples of the target molecules that react with these living body molecules can specifically include antigens bound to these antibodies, coenzymes bound to these enzymes, proteins or DNAs bound to these DNAs, and the like. In other words, it is possible for the surface plasmon resonance sensor of the present invention to utilize a protein interaction, an antibody-antigen reaction, a gene reaction, and the like, which are generally used in the conventional biosensors, to thereby use techniques such as sandwich immunoassay, an avidin-biotin reaction system, and hybridization. The surface plasmon resonance sensor can measure a quantity of these target molecules contained in the measurement sample. It is preferable that emitted beam 21 is detected at detection unit 20 in a state where aggregates made of these living body molecules and these target molecules are fixed to the surface of metal layer 4. Further, the measurement sample may be in a liquid state or a gaseous state.

Further, receptors intended for a specific olfactory sense may be fixed to metal layer 4, as the above-described living body molecules. A surface plasmon resonance sensor provided with sensor main body 50 to which these receptors intended for an olfactory sense are fixed can be utilized as a mimic living body that achieves efficiency approximately equivalent to that of a living body where in-vivo reactions occur. These receptors can be obtained by using gene analysis and manipulation techniques, or through extraction from a living body. In the present invention, refined receptors with high purity are preferably used as these receptors. In fixing these receptors to metal layer 4, antibodies or the like may simultaneously be used.

Further, the surface of this metal layer 4 for fixing these living body molecules to metal layer 4 is preferably subjected to a molecular modification process. For example, in this molecular modification, it is preferable to carry out a process of fixing molecules such as alkylsilane or alkanethiol, or molecules such as ionic polymers, to this surface. Further, each of these molecules preferably has at least one of —COOH, —$NH_2$, —$CF_3$, —$CH_3$, —CN, —$SO_3H$, and the like, as a terminal functional group. For this molecular modification process, various known techniques are selected for use.

Further, the target molecules in the measurement sample are preferably modified with nanoparticles. It is preferable that these nanoparticles contain at least one of gold, silver, aluminum, copper, titanium, nickel, and chromium, and have an average particle diameter ranging from 1 nm to 1 µm. By binding, for example, these nanoparticles to these target molecules for modification, the target molecules in the measurement sample can be sensed at metal layer 4 with higher precision. Further, by allowing a material of metal layer 4 to be different from a material of these nanoparticles, surface plasmon resonance can be amplified. Note that a known method can be used to modify these target molecules with these nanoparticles.

A material of substrate 1 is preferably made of any material selected from $SiO_2$, GaAs, InP, Si, glass, quartz, silicone, and plastic. Examples of the glass can include porous glass and the like, and examples of the plastic can include polyurethane, porous styrene, and the like.

Further, examples of a laser serving as light source 10 can include a semiconductor laser, an organic laser, and the like. As the organic laser, it is possible to use a laser described in, for example, Hajime Nakanotani et al. "Extremely low-threshold amplified spontaneous emission of 9,9'-spirobifluorene derivatives and electroluminescence from field-effect transistor structure" Adv. Funct. Mater., (in press 2007). If the present embodiment is provided with an organic laser, it is less likely to contaminate the environment when the surface plasmon resonance sensor is discarded. Note that a light source other than the laser, such as a light-emitting diode, may also be used as light source 10. Further, a laser beam emitted by this laser preferably has a wavelength ranging from 400 nm to 1600 nm. Further, in the present embodiment, 10% to 40% of laser beam 11 emitted by this laser is ejected to an outside of sensor main body 50, without being incident on metal layer 4. Therefore, intensity of this laser beam 11 is preferably set in consideration of a loss caused by the beam ejected to the outside.

<<Operation>>

A description will now be made based on FIG. 1 and FIG. 2. In the surface plasmon resonance sensor of the present invention, when laser beam 11 is introduced into metal layer 4 from its one end as described above, a surface plasmon wave 15, which is a type of surface plasmon resonance, is generated at opposite surfaces of this metal layer 4. In other words, by a new method of directly introducing laser beam 11 into metal layer 4 that serves as a waveguide, changes in refractive index at the surface of metal layer 4 can be measured over time. Changes in refractive index are measured in the opening. At the surface of metal layer 4 in the opening, as a reaction between the living body molecules fixed to this surface and the target molecules proceeds, a difference between a refractive index of first dielectric layer 2 and a refractive index of the surface of metal layer 4 is increased, and a propagation loss is increased accordingly. By measuring intensity of the beam attenuated by the propagation loss, and comparing the measured intensity with a quantity of beam in an initial state, it is possible to determine a refractive index of the surface (the periphery of the upper surface) of metal layer 4, from which it is possible to determine a quantity of target molecules that have reacted with these living body molecules, such as a quantity of antigen-antibody reactions. Further, if target molecules in the measurement sample are modified with nanoparticles, the similar phenomenon occurs in an amplified manner, so that a quantity of target molecules that have reacted with these living body molecules can be sensed with much higher sensitivity.

The surface plasmon resonance sensor of the present invention can generate a surface plasmon wave 15 by means of metal layer 4 formed into a thin film, and hence can easily be downsized. This surface plasmon wave 15 is superior in resonance sensitivity when compared with the conventional surface plasmon resonance. Therefore, the surface plasmon resonance sensor of the present invention is expected to achieve further improvement in sensitivity.

In the present embodiment, as a quantity of antigens 6 bound to antibodies 5 is increased, a refractive index of laser beam 11 that passes through metal layer 4 in this opening changes over time, and hence intensity of surface plasmon resonance that occurs at this metal layer 4 also changes. Detection unit 20 can analyze emitted beam 21 emitted from an end portion of metal layer 4 that serves as a waveguide, and calculate a quantity of antigens 6 in the measurement sample.

The surface plasmon resonance sensor in another embodiment, provided with the components as described above, will now be described. Note that the above-described materials and others can be selected as appropriate in the embodiment below.

Second Embodiment

Figure 3:
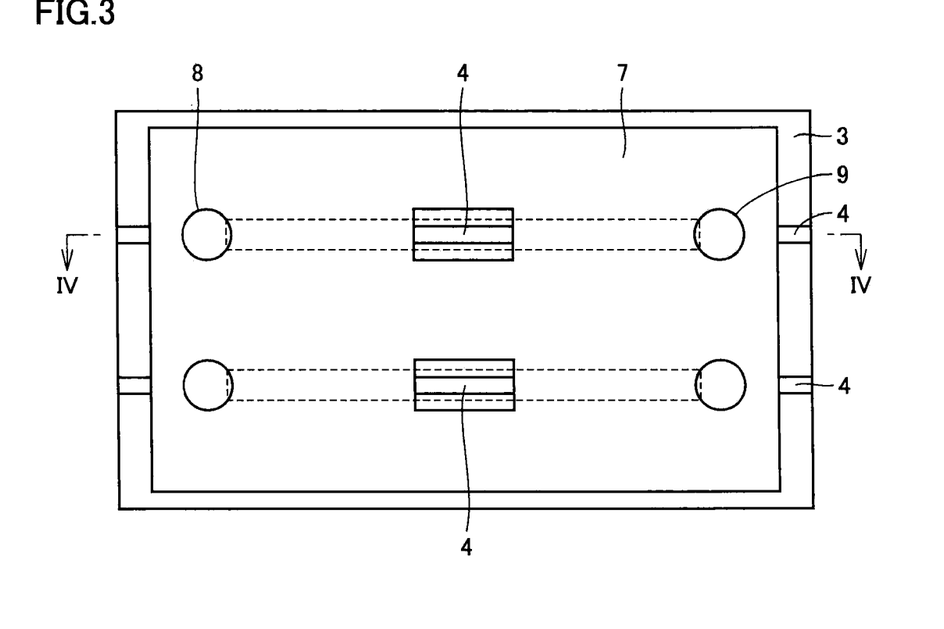
FIG. 3 is a top view that shows another embodiment of the surface plasmon resonance sensor of the present invention.
Figure 4:
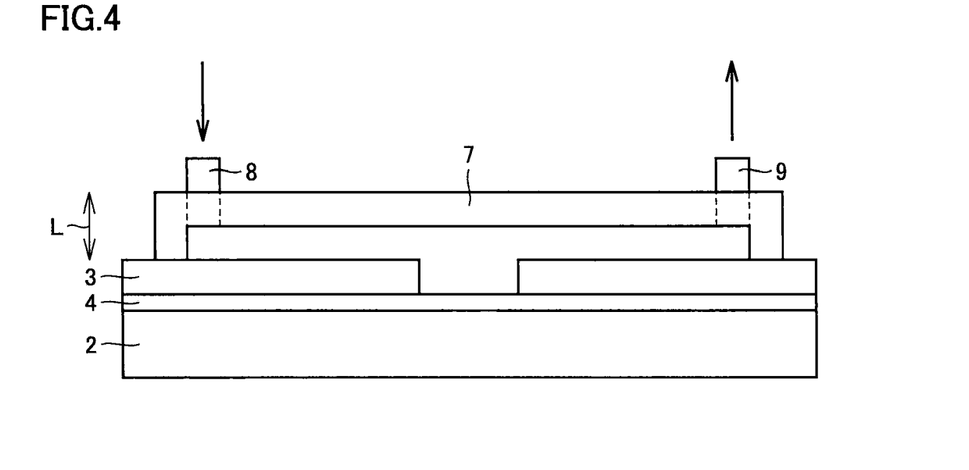
FIG. 4 is a cross-sectional view taken along a line IV-IV in FIG. 3.

FIG. 3 is a top view that shows another embodiment of the surface plasmon resonance sensor of the present invention. FIG. 4 is a cross-sectional view taken along a line IV-IV in FIG. 3. A description will now be made based on FIG. 3 and FIG. 4.

As shown in FIG. 3 and FIG. 4, a cover 7 is provided on second dielectric layer 3 in the present embodiment. Cover 7 has an inlet port 8 and an outlet port 9. The measurement sample can be introduced through inlet port 8, and this measurement sample follows a path formed by cover 7, passes by the opening, and is discharged from outlet port 9. This measurement sample is brought into contact with the living body molecules fixed to metal layer 4 in the opening of second dielectric layer 3. A rate (flow rate) at which this measurement sample is introduced into cover 7 and discharged therefrom can be selected as appropriate in accordance with a type of the measurement sample. Further, a length L in FIG. 4 can be set in accordance with a condition such as whether the measurement sample is in a gaseous state or a liquid state.

Third Embodiment

Figure 5:
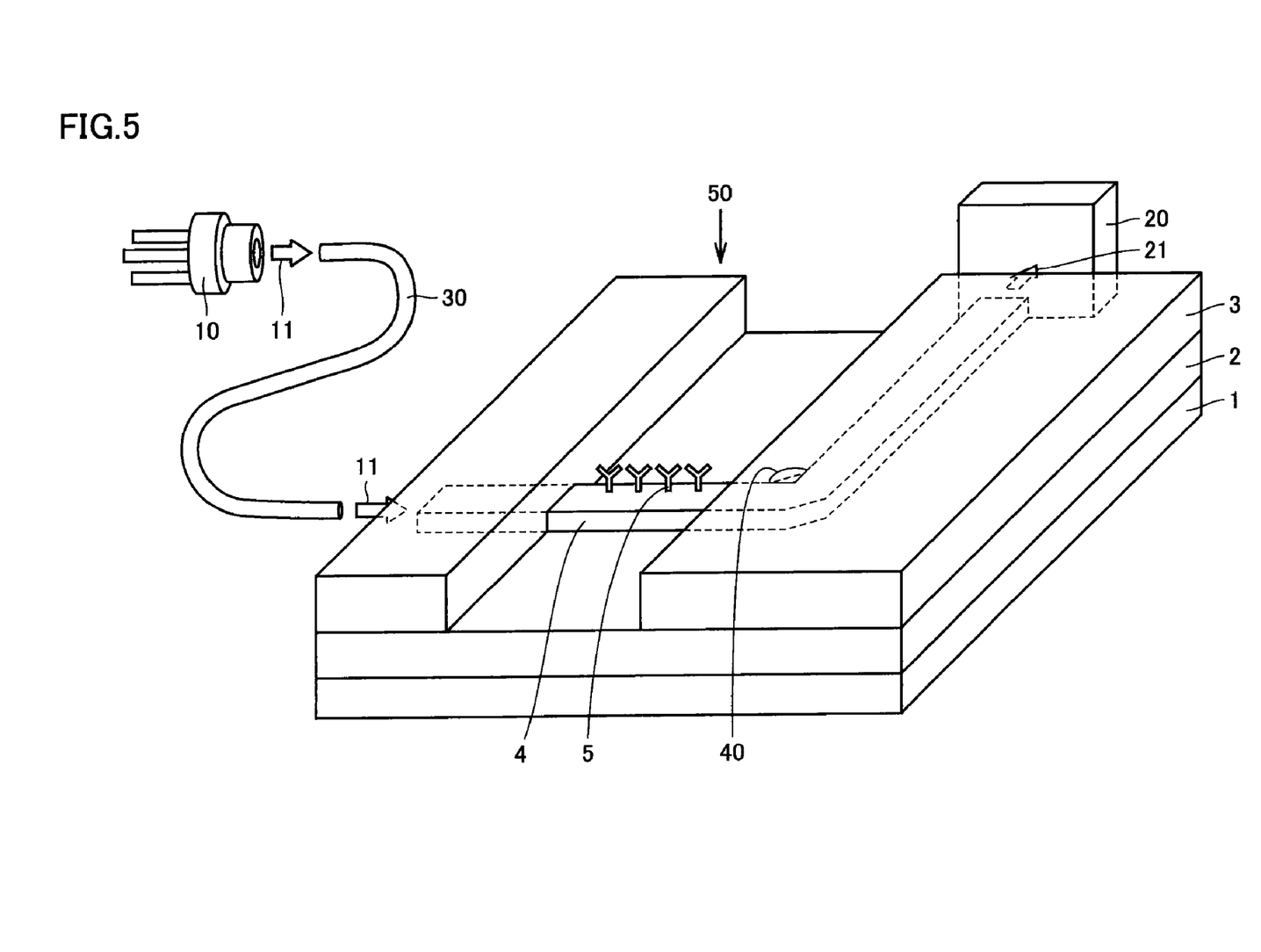
FIG. 5 is a perspective view that shows still another embodiment of the surface plasmon resonance sensor of the present invention.

FIG. 5 is a perspective view that shows still another embodiment of the surface plasmon resonance sensor of the present invention. A description will now be made based on FIG. 5.

As shown in FIG. 5, a direction along which incident beam 11 emitted from laser 10 travels may not be identical to a direction along which beam 21 emitted from metal layer 4 travels. For example, incident beam 11 emitted from laser 10 may be introduced into metal layer 4 through an optical fiber 30. Further, metal layer 4 may be formed to have an approximately L-shape. At this time, an angle 40 in FIG. 5 may be adjusted to fall within a range of, for example, 0° to 90°. In the surface plasmon resonance sensor, it is preferable that a direction along which incident beam 11 travels, and a direction along which emitted beam 21 travels are not collinear, so as not to detect stray light.

Fourth Embodiment

It is possible to fabricate a biochip provided with the surface plasmon resonance sensor fabricated in the third embodiment. The surface plasmon resonance sensor of the present invention can extremely be downsized when compared with the conventional one, and hence it is possible to fabricate a biochip provided with this surface plasmon resonance sensor. A setting may be made as appropriate such that laser 10, sensor main body 50, and detection unit 20 in the surface plasmon resonance sensor, and a device and the like for supplying them with electric power and the like, are accommodated as appropriate on a single biochip.

If an organic laser is used as laser 10, for example, and silicon is used for first dielectric layer 2 and second dielectric layer 3 in this biochip, it is possible to provide an economically-disposable biochip less likely to contaminate the environment when being discarded.

The present invention will hereinafter be described in further detail by citing examples. However, the present invention is not limited thereto.

First Example

Surface Plasmon Resonance Sensor which Utilizes Antigen-Antibody Reactions

<<Fabrication of Surface Plasmon Resonance Sensor>>

A description will now be made based on FIG. 1. In the present example, sensor main body 50 formed of first dielectric layer 2 made of $SiO_2$, metal layer 4 made of gold, and second dielectric layer 3 made of $SiO_2$ was provided on substrate 1 made of silicon. For metal layer 4, a layer having a thickness of 15 nm, a length in a transverse direction of 8 µm, and a length in a longitudinal direction of 2 mm was used. Further, the opening provided in second dielectric layer 3 was formed to have a length in a longitudinal direction of 1 mm, and a length in a transverse direction of 10 µm.

Figure 6:
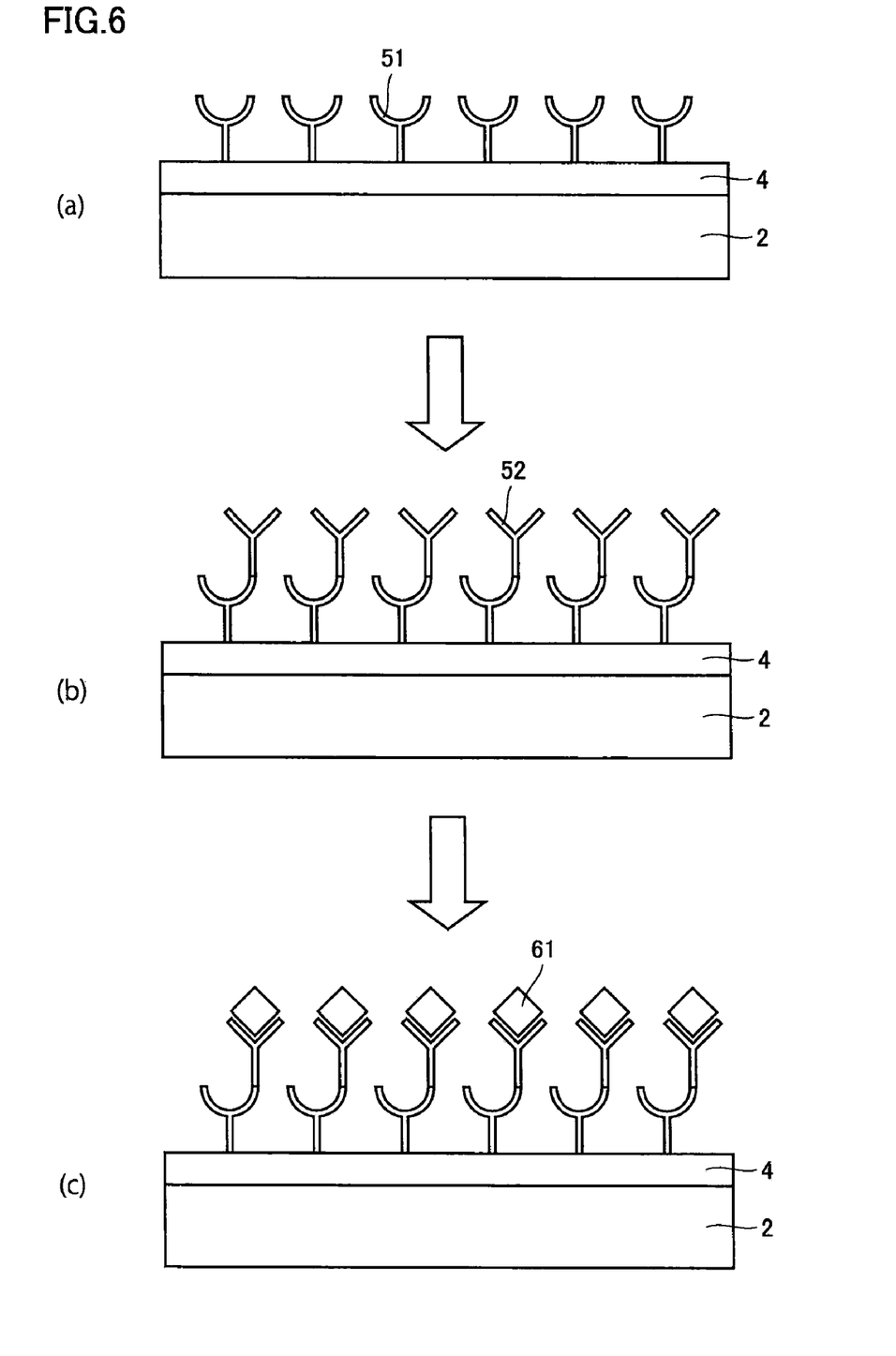
FIG. 6 is a schematic view that shows an antigen-antibody reaction in a first example.

Here, FIG. 6 is a schematic view that shows an antigen-antibody reaction in the present example. A description will now be made based on FIG. 6. Initially, as shown in FIG. 6(a), primary antibodies 51 (Anti mouse IgG antibodies) were fixed onto metal layer 4. A process of fixing primary antibodies 51 was carried out in the following steps from (1) to (3).

(1) Cleaning of the metal layer: the surface of metal layer 4 was cleaned for 10 minutes with a sulfuric acid-hydrogen peroxide water mixture (4:1) at 120° C. Subsequently, sensor main body 50 was soaked in a 10 mmol/L ethanol solution of MUA (mercaptoundecanoic acid) for 24 hours. After the soakage, the surface of metal layer 4 of that sensor main body 50 was cleaned with pure water. That sensor main body 50 was then subjected to ultrasonic cleaning in ethanol for 10 minutes, cleaned with pure water, and dried in a nitrogen atmosphere.

(2) A molecular modification process for fixing antibodies: the surface of metal layer 4 in that sensor main body 50 was subjected to a molecular modification process. Initially, sensor main body 50 after step (1) was soaked in 100 mL of a 100 mg/ml aqueous solution of NHS (N-hydroxysuccinic acid imide). Subsequently, to the NHS aqueous solution, 100 mL of a 100 mg/ml aqueous solution of EDC (N-(3-dimethylaminopropyl)-N'-ethylcarbodiimide) was added, and the obtained mixture was let stand for one hour in an agitated condition. The surface of metal layer 4, which had been subjected to molecular modification, was cleaned with pure water, and then cleaned with a 0.1 mol/L Tris-hydrochloric acid buffer solution (TBS, pH 8.0). On the surface of metal layer 4, which had become active after the molecular modification process, 90 µL of a Tris-hydrochloric acid buffer solution was allowed to drip.

(3) Fixing of antibodies: 120 seconds after step (2), 10 µL of an antibody solution, which is a solution obtained by diluting primary antibodies 51 with a 0.1 mol/L TBS by a factor of 25, was allowed to drip on the surface of metal layer 4. Thirty minutes after the dripping, that surface was cleaned with the TBS, and then 100 µL of the 0.1 mol/L TBS was allowed to drip on that surface. Finally, 100 µL of an aqueous solution of ethanolamine was allowed to drip on the surface of metal layer 4, where primary antibodies 51 were fixed, and the surface was then let stand for one hour. With that ethanolamine aqueous solution, the surface of metal layer 4 where no antibodies were fixed was made inert.

Next, as shown in FIG. 6(b), Anti FLAG monoclonal antibodies, which served as secondary antibodies 52, were bound to primary antibodies 51, and fixed to the surface of that metal layer 4. A process of fixing secondary antibodies 52 was carried out in the following procedure.

Initially, the surface of metal layer, where primary antibodies 51 had been fixed, was cleaned with pure water, and then further cleaned with a Hepes buffer solution (HBS, pH 7.4). A channel pattern (made of silicone) for delivering that Hepes buffer solution was disposed on the surface of metal layer 4. Then 25 µg/mL secondary antibodies 52 were delivered into that channel pattern for 10 minutes. Through such a manipulation, the Anti FLAG antibodies were fixed to the surface of metal layer 4.

<<Measurement>>

Finally, as shown in FIG. 6(c), secondary antibodies 52 were brought into contact with a measurement sample that contained FLAG-BAPs (control proteins), which were identified as antigens 61, and a quantity of antigens 61 contained in that measurement sample was measured. Initially, the HBS was delivered, and then the measurement sample adjusted by the HBS such that FLAG-BAPs achieved a concentration of 25 µg/ml, was delivered into the above-described channel pattern for five minutes. After the delivery of the measurement sample, the HBS was delivered again. At that time, a semiconductor laser that emits a beam having a wavelength of 1500 nm was used as light source 10.

Figure 7:
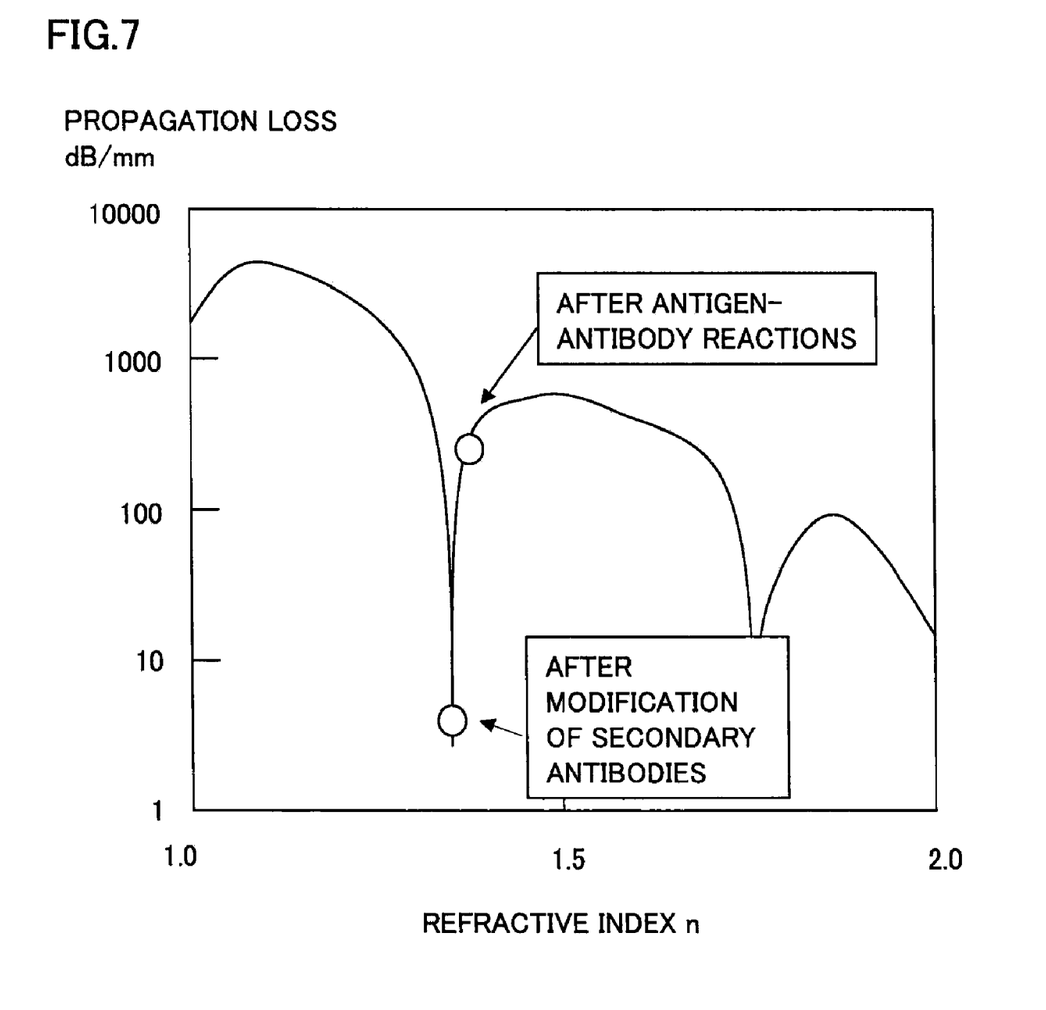
FIG. 7 is a diagram that shows a result of measurement by the surface plasmon resonance sensor in the first example.

FIG. 7 is a diagram that shows a result of measurement by the surface plasmon resonance sensor in the first example. In FIG. 7, the axis of abscissas indicates changes in refractive index of a periphery of the upper surface of metal layer 4, and the axis of ordinates indicates a value of a propagation loss calculated from intensity of each of an incident beam and an emitted beam, and a traveling distance of that incident beam. As shown in FIG. 7, before delivery of the measurement sample, namely, immediately after fixation of secondary antibodies 52, a propagation loss was 2.3 dB/mm. However, after delivery of that measurement sample, in other words, after antigen-antibody reactions, a propagation loss was 220 dB/mm. This shows that significant changes in propagation loss can be observed owing to binding between antigens 61 and secondary antibodies 52.

As shown in FIG. 7, which explanatorily shows the result, changes in refractive index of a periphery of the surface of metal layer 4 cause significant changes in propagation loss in laser beam 11 in the surface plasmon resonance sensor. In the antigen-antibody reactions in the present example, it is known that a refractive index of a periphery of the surface of metal layer 4 varies before and after the antigen-antibody reactions. Therefore, by observing changes in propagation loss, it is possible to monitor interactions between the living body molecules fixed to the surface of metal layer 4 and the target molecules contained in the measurement sample, by means of detection unit 20.

Second Example

Surface Plasmon Resonance Sensor Serving as Olfactory Sensor

Figure 8:
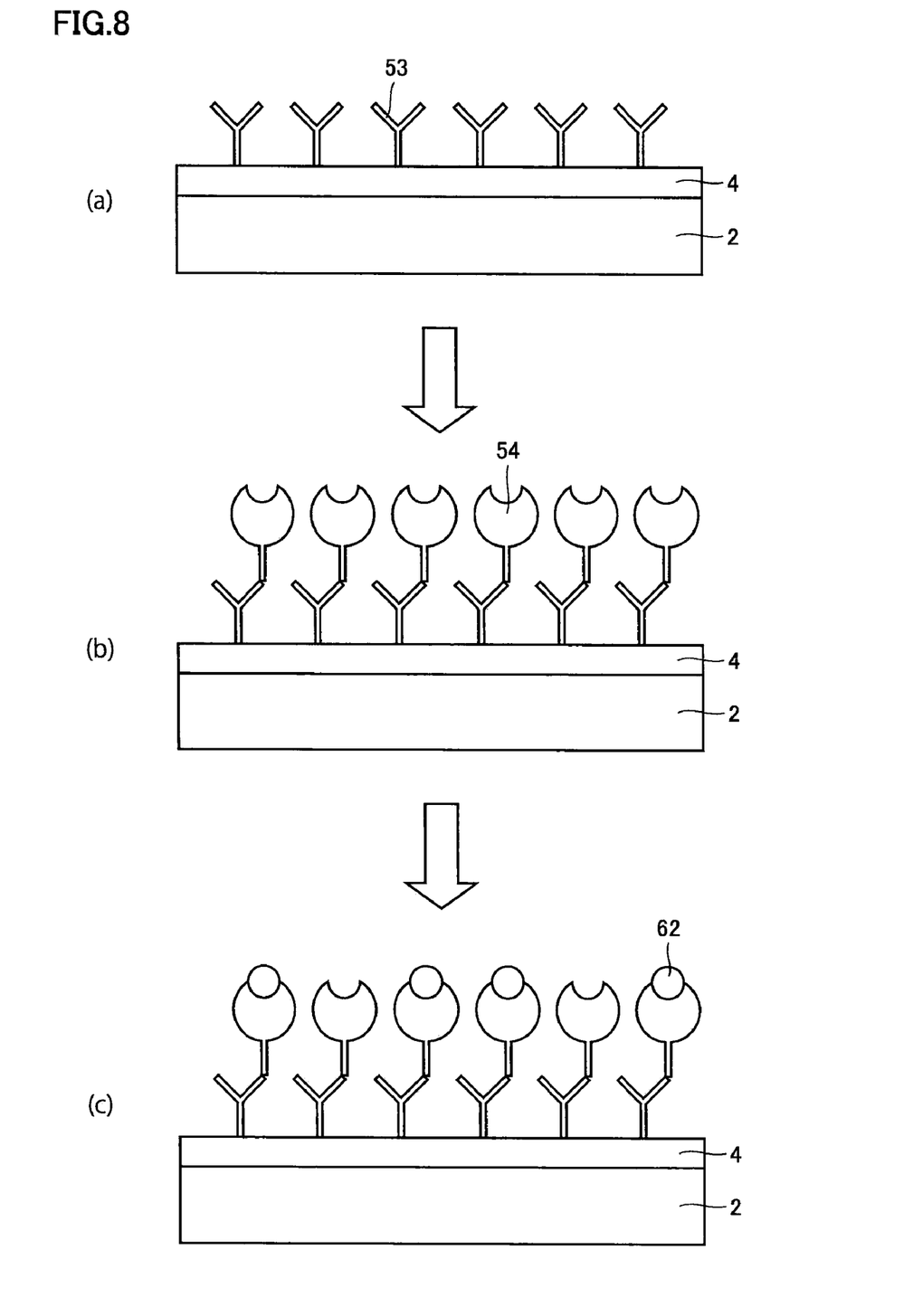
FIG. 8 is a schematic view that shows a reaction in a second example.

FIG. 8 is a schematic view that shows a reaction in the present example. A description will now be made based on FIG. 8.

A step of fixing antibodies 53 (Anti His (histidine) antibodies) onto metal layer 4, as shown in FIG. 8(a), was carried out as in the manipulation in the first example.

Next, as shown in FIG. 8(b), receptors 54 were bound to antibodies 53, to thereby fix receptors 54 to metal layer 4. At that time, a manipulation similar to that in the first example was conducted, except that odorous substance receptors each having a His (histidine) tag were used as receptors 54.

<<Measurement>>

Finally, as shown in FIG. 8(c), receptors 54 were brought into contact with a measurement sample that contained odorous substances 62, and a quantity of odorous substances 62 contained in that measurement sample was measured. Initially, the HBS was delivered, and then the measurement sample adjusted by the HBS such that odorous substances 62 achieved a concentration of 10 µM, was delivered into the above-described channel pattern for two minutes. After the delivery of the measurement sample, the HBS was delivered again. At that time, a semiconductor laser that emits a beam having a wavelength of 1500 nm was used as light source 10.

Figure 9:
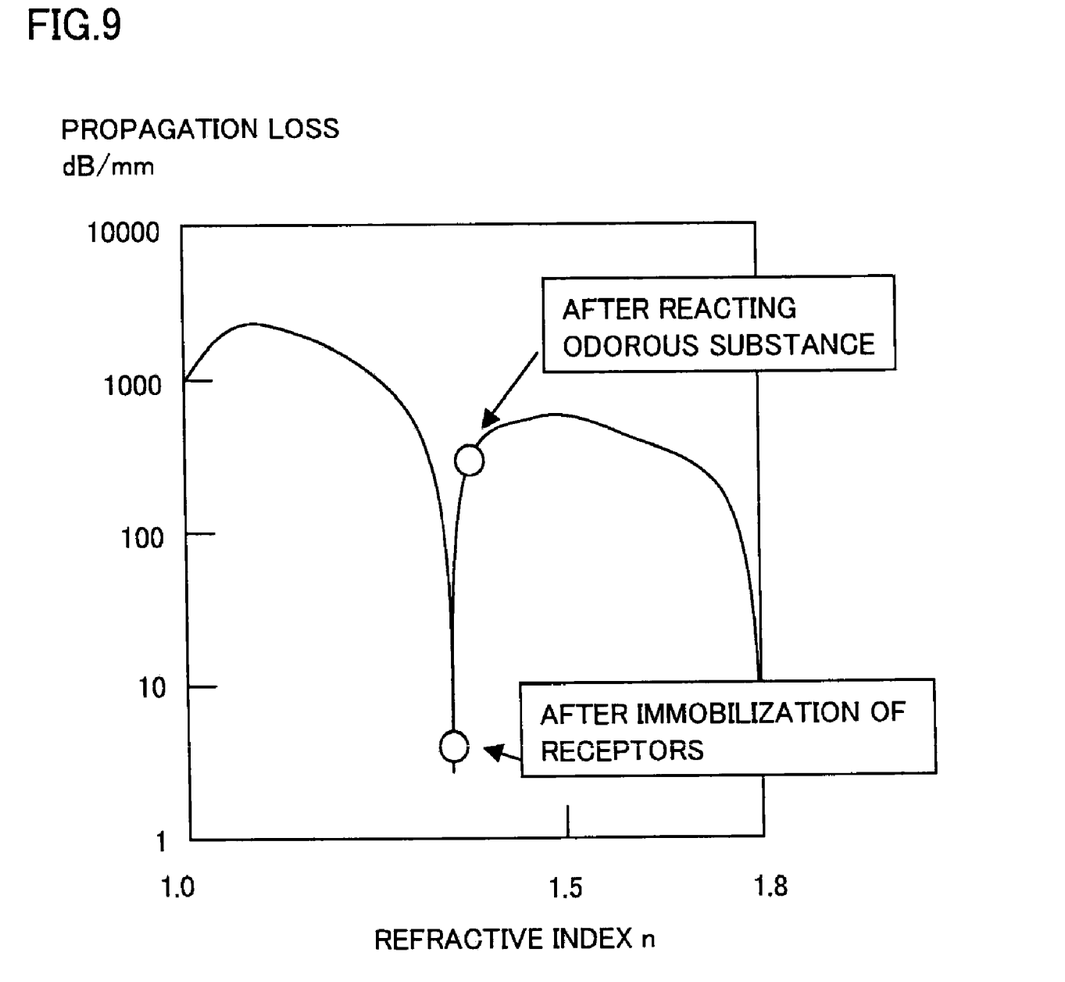
FIG. 9 is a diagram that shows a result of measurement by the surface plasmon resonance sensor in the second example.

FIG. 9 is a diagram that shows a result of measurement by the surface plasmon resonance sensor in the second example. In FIG. 9, the axis of abscissas indicates changes in refractive index of a periphery of the surface of metal layer 4, and the axis of ordinates indicates a value of a propagation loss calculated from intensity of each of an incident beam and an emitted beam. As shown in FIG. 9, before delivery of the measurement sample, namely, immediately after fixation of receptors 54, a propagation loss was 2.5 dB/mm. However, after delivery of that measurement sample, in other words, after odorous substance reactions, a propagation loss was 250 dB/mm. This shows that significant changes in propagation loss can be observed owing to binding between odorous substances 62 and receptors 54.

As shown in FIG. 9, which explanatorily shows the result, changes in refractive index of a periphery of the surface of metal layer 4 cause significant changes in propagation loss in laser beam 11 in the surface plasmon resonance sensor. In the antigen-antibody reactions in the present example, it is known that a refractive index of a periphery of the surface of metal layer 4 varies before and after those antigen-antibody reactions. Therefore, by observing changes in propagation loss, it is possible to monitor interactions between the living body molecules fixed to the surface of metal layer 4 and the target molecules contained in the measurement sample, by means of detection unit 20.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A surface plasmon resonance sensor which has a first dielectric layer, a metal layer disposed on said first dielectric layer, and a second dielectric layer covering said metal layer, the surface plasmon resonance sensor comprising:
    a sensor main body provided with an opening for exposing a part of a surface of said metal layer on a side facing said second dielectric layer, and for allowing a measurement sample to be brought into contact with the surface;
    a light source for introducing a beam into said metal layer from one end of said metal layer; and
    a detection unit detecting a beam emitted from the other end of said metal layer.

2. The surface plasmon resonance sensor according to claim 1, wherein said metal layer is made of any of materials selected from gold, silver, aluminum, copper, titanium, nickel, and chromium.

3. The surface plasmon resonance sensor according to claim 1, wherein said metal layer has a thickness ranging from 1 nm to 100 nm.

4. The surface plasmon resonance sensor according to claim 1, wherein a refractive index of each of said first dielectric layer and said second dielectric layer falls within a range of 1.0 to 4.0.

5. The surface plasmon resonance sensor according to claim 1, wherein said sensor main body is provided on a substrate made of any of materials selected from $SiO_2$, GaAs, InP, Si, glass, quartz, silicone, and plastic.

6. The surface plasmon resonance sensor according to claim 1, wherein living body molecules are fixed onto said metal layer in the opening of said second dielectric Layer, and said measurement sample is brought into contact with said living body molecules.

7. The surface plasmon resonance sensor according to claim 6, wherein
    target molecules contained in said measurement sample and reacting with said living body molecules are modified with nanoparticles, and
    said nanoparticles contain at least one of gold, silver, aluminum, copper, titanium, nickel, and chromium, and have an average particle diameter ranging from 1 nm to 1 µm.

8. The surface plasmon resonance sensor according to claim 6, wherein aggregates made of said living body molecules and said target molecules are fixed to the surface of said metal layer.

9. A biochip provided with the surface plasmon resonance sensor recited in claim 1.

* * * * *